(12) United States Patent
Schulze et al.

(10) Patent No.: US 6,443,890 B1
(45) Date of Patent: Sep. 3, 2002

(54) WIRELESS INTERNET BIO-TELEMETRY MONITORING SYSTEM

(75) Inventors: Arthur E. Schulze, Wharton, TX (US);
Tommy G. Cooper, Friendswood, TX (US); Emil S. Macha, Sugar Land, TX (US)

(73) Assignee: i-Medik, Inc., Santa Fe, NM (US)

( * ) Notice: Subject to any disclaimer, the term of this patent is extended or adjusted under 35 U.S.C. 154(b) by 0 days.

(21) Appl. No.: 09/516,645

(22) Filed: Mar. 1, 2000

(51) Int. Cl.[7] ................................. A61B 5/00
(52) U.S. Cl. .................. 600/300; 128/903; 128/904; 128/920; 600/301
(58) Field of Search .................. 128/904, 903, 128/900, 897–898, 920–925; 600/300–301, 481, 500, 529, 549, 545; 702/2–3

(56) References Cited

U.S. PATENT DOCUMENTS

| | | | | |
|---|---|---|---|---|
| 5,515,858 A | * | 5/1996 | Myllymaki | 600/503 |
| 5,544,661 A | * | 8/1996 | Davis et al. | 600/300 |
| 5,673,692 A | * | 10/1997 | Schulze et al. | 600/301 |
| 5,678,562 A | * | 10/1997 | Sellers | |
| 6,168,563 B1 | * | 2/2001 | Brown | 600/301 |
| 6,225,901 B1 | * | 5/2001 | Kail, IV | 128/904 |
| 6,231,519 B1 | * | 5/2001 | Blants et al. | 600/529 |
| 6,264,614 B1 | * | 7/2001 | Albert et al. | 600/528 |
| 6,292,573 B1 | * | 9/2001 | Zurek et al. | |
| 6,292,698 B1 | * | 9/2001 | Duffin et al. | 607/32 |

* cited by examiner

Primary Examiner—Kevin Shaver
Assistant Examiner—Michael C Astorino
(74) Attorney, Agent, or Firm—Roberts, Abokhair & Mardula, LLC

(57) ABSTRACT

A system and method for monitoring patient variables in a wireless mode via a patient worn monitoring devices. The patient worn monitoring device connects to a variety of bio-sensors with at least one microphone for voice communications. The pertinent worn device connects to a wireless network and thence to the internet for transmitting voice and data to a health care provider. The health care provider communicates with the patient worn device via the internet and the wireless network to send instructions to the patient worn monitoring unit and to communicate via voice with the patent. The health care provider can also flexibly reconfigure the patent worn monitoring device to change collection parameters for the bio-sensors worn by the patient. When an alarm limit is exceeded an detected by the bio-sensors, it is transmitted to the health care provider over the wireless network and thence over the internet thereby allowing full mobility to the patient wearing the device.

14 Claims, 3 Drawing Sheets

WIRELESS INTERNET BIO-TELEMETRY MONITORING SYSTEM

FIELD OF THE INVENTION

This invention relates generally to medical monitoring devices. More particularly the present invention is a system and method for monitoring physiologic variables of an individual in a wireless mode over the Internet.

BACKGROUND OF THE INVENTION

Monitoring devices of various types to monitor patient physiologic conditions have long been in the medical community. A plethora of testing and monitoring equipment have moved out of the hospital into the doctors' offices and, in some cases have even progressed into home monitoring systems.

While these devices have clearly been extremely useful, many of these devices require that a patient be located at home, or in close proximity to a telephone system such that results of the monitoring can be transmitted over the public switch telephone network (PSTN) to some form of analysis center. Such devices do not necessarily lend themselves to the mobile life style in which many individuals find themselves.

For example, it is difficult for a busy person to stop in the middle of the day, proceed to a monitoring station, whether it be a home or in some office, take the appropriate measurements, is and then proceed with the business of the day. This is simply not possible and adds a level of stress to the already stressful situation of having to monitor physiologic signals.

What would be truly useful is a system for monitoring physiologic characteristics of an individual on a mobile basis. Such a system would require little if any interaction with a monitoring device. Signals that are collected would then be sent in an automated fashion to an analysis center or a physician's office. Alternatively a physician could interrogate the system worn by a patient while the patient is mobile to obtain the physiologic signals of interest.

SUMMARY OF THE INVENTION

It is therefore an objective of the present invention to remotely monitor physiologic variables from any patient.

It is a further objective of the present invention to monitor physiologic variables of a patient whether the patient is ambulatory or stationary when the physician is remote from the patient.

It is yet another objective of the present invention to monitor physiologic variables using the Internet.

It is a further objective of the present invention to monitor physiologic variables in a wireless manner within a generalized geographic area.

It is further objective of the present invention to monitor physiologic variables without the patient having to proceed to any centralized location in a geographic area.

It is further objective of the present invention to monitor a patient anywhere in the coverage map of a cellular or satellite based telephone network.

It is further objective of the present invention to have data relating to physiologic variables automatically sent over a wireless network to a physician or other medical caregiver.

It is further objective of the present invention to allow a physician to interrogate the physiologic monitoring device in a wireless fashion whenever the physician needs to take such physiologic measurements.

It is further objective of the present invention to provide to a voice communications in a wireless mode to a medical caregiver.

It is further objective of the present invention to have a "panic" function which allows both a user to send a "panic" message to a physician or allow a physician, after monitoring physiologic signals, to send a voice "advice" message to the patient.

It is further objective of the present invention to accomplish all the above objectives using a device that is worn by the patient in a relatively unobtrusive fashion.

These and other objectives of the present invention will become apparent to those skilled in the art from a review of the specification that follows.

The present invention is a wireless Internet bio-telemetry monitoring system (WIBMS). The system makes use of a variety of bio-sensors which are generally used to detect signals or variables from the human body. One such sensor system is described in U.S. Pat. No. 5,673,692 whose characteristics are incorporated herein by reference in their entirety, wherein a single site, multi-variable patient monitoring apparatus for monitoring multiple physiological variables of a patient at a single site on the patient is disclosed for ambulatory monitoring, home monitoring, procedure monitoring and similar situations. The apparatus has an infrared (IR) temperature sensor, a pulse oximeter sensor and a communication circuit for outputting information produced from the pulse oximeter and information produced from the infrared temperature measuring device. These elements are integrally placed within a mold or plug made to fit the ear of the patient. However, this particular sensor is not meant as a limitation. Literally any type of bio-sensor generally known to those skilled in the art will find use in the present invention. Further the sensor of U.S. Pat. No. 5,673,692 can further be modified to include a microphone so that voice of the patient can be transmitted using the system of the present invention.

The bio-sensors are connected to a combination data acquisition module and wireless transceiver which is worn by the patient. This combination sensor package and communication unit is known as the multi-variable patient monitor, or MVPM. The MVPM is battery powered. The batteries that power the MVPM can be single use batteries or rechargeable batteries. Further, when the individual is in a mobile state, the batteries of the MVPM can be recharged by plugging into a car or into normal wall current. This allows the individual to constantly keep batteries charged in the MVPM whether the individual is mobile or in an office.

As noted above, the MVPM is a combination patient-worn device which allows maximum mobility to the particular patient.

The MVPM has the ability, on a periodic basis, to interrogate bio-sensors worn by the patient and to store physiologic signals from the bio sensors. On a periodic basic, the MVPM calls into a wireless network and transmits the bio-sensor information to the wireless network. The bio-sensor information then proceeds from the wireless network to the Internet and then to an analysis center or a data warehouse which receives and stores the information for subsequent analysis.

The MVPM also comprises an emergency "panic" button whereby a patient can direct the transceiver portion of the MVPM to automatically call 911 in the event of a medical emergency.

As noted above, the MVPM is connected to various bio-sensors. Therefore the MVPM has sensor condition detection circuitry, connected to a lamp, which allows a user to determine that all sensors are operating correctly. When a senor receives a particular signal which is out of the normal physiologic range for the particular patient, an alarm sound and light are actuated such that the individual can understand that a significant medical event is occurring. Simultaneously with such an alarm, a time-tagged signal is sent to the medical care provider notifying the provider of the event.

Thus, when the MVPM is functioning in a data acquisition mode, it receives information from the sensors, performs some limited analysis on that information and has the ability to notify the patient of any non-standard conditions.

When the MVPM periodically sends stored signals from the bio sensor over the network a unique identifier is associated with any such data that is sent such that the data can be directly associated with a particular patient.

Once data are received at the server, the data are stored with appropriate privacy and security issues dealt with in a manner known to those skilled in the art.

The MVPM also comprises circuitry for self testing its various sub systems and sensors and for communicating any trouble shooting information directly to the patient in the event that the sensor becomes dislodged or non-functional. Further, such trouble shooting data can also be sent in a wireless mode to the central server such that trouble shooting can take place remotely, or in the alternative, a new MVPM unit can be sent to the patient.

The MVPM also can be preset before giving it to a patient. In addition, and depending upon the biological signals being monitored, alarms can be set remotely by the health care provider over the internet and subsequently via the wireless network and can be based upon the caregiver's knowledge of the condition of the patient. Such remote setting also occurs via the two way communication of the transceiver portion of the MVPM.

Communication rates of the WIBMS are optimized to fit common cellular calling and rate plans and to minimize the cost and air time usage.

Using the WIBMS the following types of monitoring can take place:
digitally sampled electrocardiogram
patient body temperature
pulse oximetry
pulse rate
other physiologic variables, such as blood glucose, respiration, etc.
various pre set alarm conditions or physiologic variables event occurrences per patient action/input.

As also noted above the MVPM has bi-directional communication capability and has the capability to transmit a "panic" signal over wireless network, to initate 911 calls, to allow a patient-initiated voice calling over a cellular telephone link, and to allow medical provider voice calling to the patient over a cellular telephone link.

Other characteristics of the present invention will become apparent to those skilled in the art by review of the detailed description of the invention that follows.

DETAILED DESCRIPTION OF THE INVENTION

As noted above the present invention is a wireless Internet bio-telemetry system comprising a patient monitoring device which is conveniently worn by a patient and which comprises bio-sensors together with a combination network that allows biologic data to be reviewed and acted upon by a health care provider who is located remotely from the patient. Data from the monitoring system are then sent in a wireless mode over a cellular network to both the public switched telephone network (PSTN) or over the Internet to a data analysis center and/or to a medical care provider.

Figure 1:
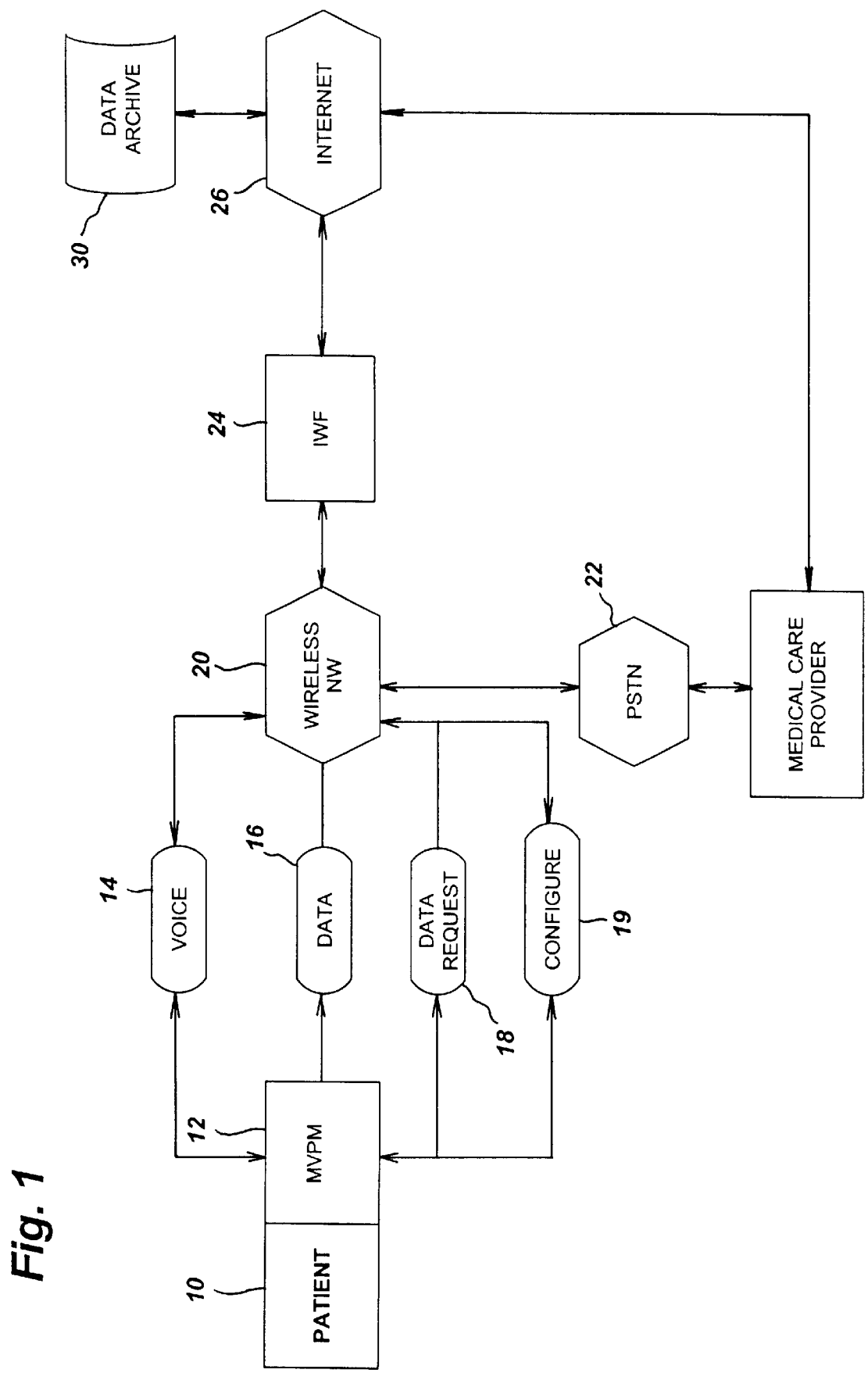
FIG. 1 illustrates the wireless Internet bio telemetry system.

Referring first to FIG. 1 the wireless Internet bio telemetry system (WIBMS) is illustrated. Patient 10 wears a multi-variable patient monitor (MVPM) 12. This MVPM monitors a variety of bio-signals as further noted below. The MVPM 12 has the capability of communicating bi-directionally via voice 14 in much the same manner as a normal cellular telephone. However, in addition, the MVPM sends data 16 on a periodic basis, or in some cases on a continuous real time basis, over a cellular network as well as receives requests for data 18 which may be made by a medical care provider over the cellular telephone network.

Cellular telephone network 20 is the normal digital cellular telephone network currently in use. This type of network is not however meant as a limitation. For example PCS networks and other types of wireless local loop networks are also suitable for transmission of the voice and data envisioned by the present invention. It will be apparent to those skilled in the art that such other networks can satisfy the requirements for transmission of voice 14, data 16, and request for data 18 to and from patient 10.

Once physiologic data is transmitted over network 20, it is then transmitted via an Internetworking Function (IWF)® 24 (for example) to, preferably the Internet 26 for subsequent communication over the Internet to the Host for retrieval and review by the medical care provider 28. In addition, data can be archived again via the Internet 26 to a data archiving and distribution facility 30 ("Host"). Data that are archived are stored in a private and secure fashion using techniques known in the art that allow secure transmission and access limitations.

In the event that voice traffic is being transmitted from the patient, a cellular network 20 connects to the public switched telephone network 22 which connects to the medical care provider (or 911 operator). Again, in this fashion, the medical care provider can receive voice information from the patient 10 and provide voice feedback to the patient as well. Similarly, the medical care provider 28 can both receive traffic from the WIBMS as well as transmit requests for data over Internet 26 through IWF 24 over the cellular network 20 through the Internet via the data repository (Host) to the MVPM 12 as well as configure 19 the WVPM.

All data that is received from the MVPM and the network is archived 30 so that the data from the specific patient can be monitored over time and so that data can be analyzed for trends that can be used for alarm setting and data collection protocols. All such data is transmitted in an encrypted and possibly non-attributable form with limited access using methods known in the art so that patient privacy and confidentiality is maintained.

Figure 2:
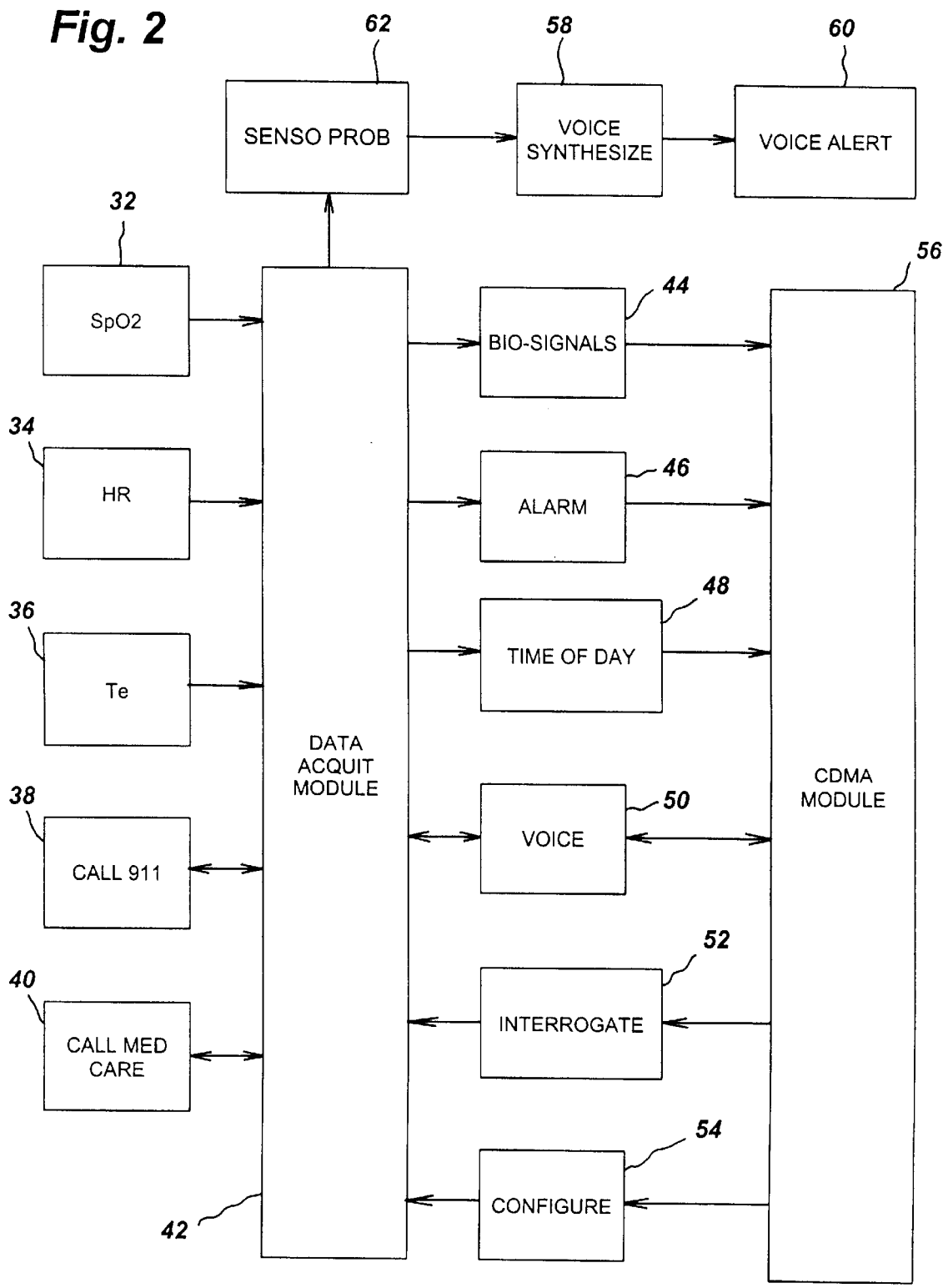
FIG. 2 illustrates the multi variable patient monitoring portion of the WIBMS

Referring to FIG. 2, the multi variable patient monitor (MVPM ) is further illustrated. The MVPM (initially noted as 12 in FIG. 1) comprises, without limitation a number of bio-sensors. For example, blood oxygen saturation level 32, pulse rate 34, and body temperature 36 can all be measured by bio sensors associated with the appropriate measurement. Signals from the sensors are picked up and stored by the data acquisition module 42. This information from the bio sensors 44 is then sent to the CDMA (although other protocols may also be used) module 56 of the MVPM for subsequent transmission.

In addition to simply acquiring data, the data acquisition module 42 also notes any alarm condition 46 and transmits that information via CDMA module 56 to the internet where it can be accessed by medical care provider. In addition, data acquisition module 42 transmits the time of day 48 with any transmission of alarm information or bio sensor information. As noted earlier, the various alarm conditions can be reconfigured by the health care provider over the internet and the wireless network without any patient interaction.

The CDMA module is for example one manufactured by Qualcomm for use with cellular telephone module. That information, in connection with 3Comm "QuickConnect" Internet connection software and 3Comm interworking function (IWF) device are all used to connect to, for example, the Sprint digital cellular telephone network. The characteristics of the Qualcom CDMA cellular phone module, the 3Comm Quickconnect Internet connection software and the 3Com interworking function device are all incorporated herein by reference in their entirety.

The CDMA module 56 allows for digital cellular communications at 14.4 kbps which is sufficient for the transmission of the bio-sensor information contemplated by the present invention. This is not however meant as a limitation as further faster wireless modulated speeds will become available. All of these faster connections will be suitable for transmission of the data and voice of the present invention.

Data that is collected is encrypted to prevent eavesdropping or tampering with any commands. All information and data is Internet protocol compatible and contains error checking to insure data accuracy.

The data acquisition module 42 continuously monitors, for example and without limitation, ECG and transmits that information from the MVPM to the Internet. Transmission of data can be in real time and/or can be stored and forwarded depending upon the collection protocol ordered by the medical service provider. Similarly, temperature measurement, pulse oximetry, and pulse rate all can be collected and transmitted continuously during various periods of time or can be collected stored and burst transmitted over the wireless network as required.

The data acquisition module contains logic that allows an "alarm" condition to be transmitted at any time whenever the alarm characteristics are fulfilled. Further, any alarm condition can be reconfigured by the health care provider via the internet and thence over the wireless network, or directly over the wireless network. Any "sensor off" signals, which are messages to both the patient and the medical service provider that, for example a sensor is turned off, broken, or has become disconnected 62 is sent upon occurrence. While such information is transmitted by the data acquisition module 42 to the CDMA module 56 and thence to the wireless network, a voice synthesizer 58 also provides a voice alert 60 to the patient that a particular alarm or sensor off condition has occurred.

As noted earlier the patient also has the ability to automatically dial 911 38 as needed. Data acquisition module 42 also processes this information and passes it over a voice connection 50 to CDMA module 56 and thereafter to the wireless network for communication.

The patient also has the ability to call the medical care provider 40 on a non-emergency basis. This is accomplished by a dedicated function "button" on the MVPM. Again, data acquisition module 42 processes voice information 50 and passes that information to the CDMA module 56.

As noted above the medical service provider or other organization that is responsible for monitoring and maintenance of the MVPM can interrogate the data acquisition module of the MVPM. In this way a request for information flows over the wireless network through the CDMA module 56 to interrogate 52 the data acquisition module 42 to provide information or to simply do a status check on the data acquisition module to insure that it is functioning appropriately. Alternatively, the data acquisition module can be reconfigured 54 to update communications capabilities, or to change the protocol for frequency of monitoring physiologic data and alarm limits.

The system of the present invention includes the network and can allow any number of MVPMs. This system is only limited by the capacity of the wireless network to handle traffic. In the same fashion that a cellular telephone has a roaming capability, so does the MVPM, therefore allowing continual transmission and updating of physiologic data.

Figure 3:
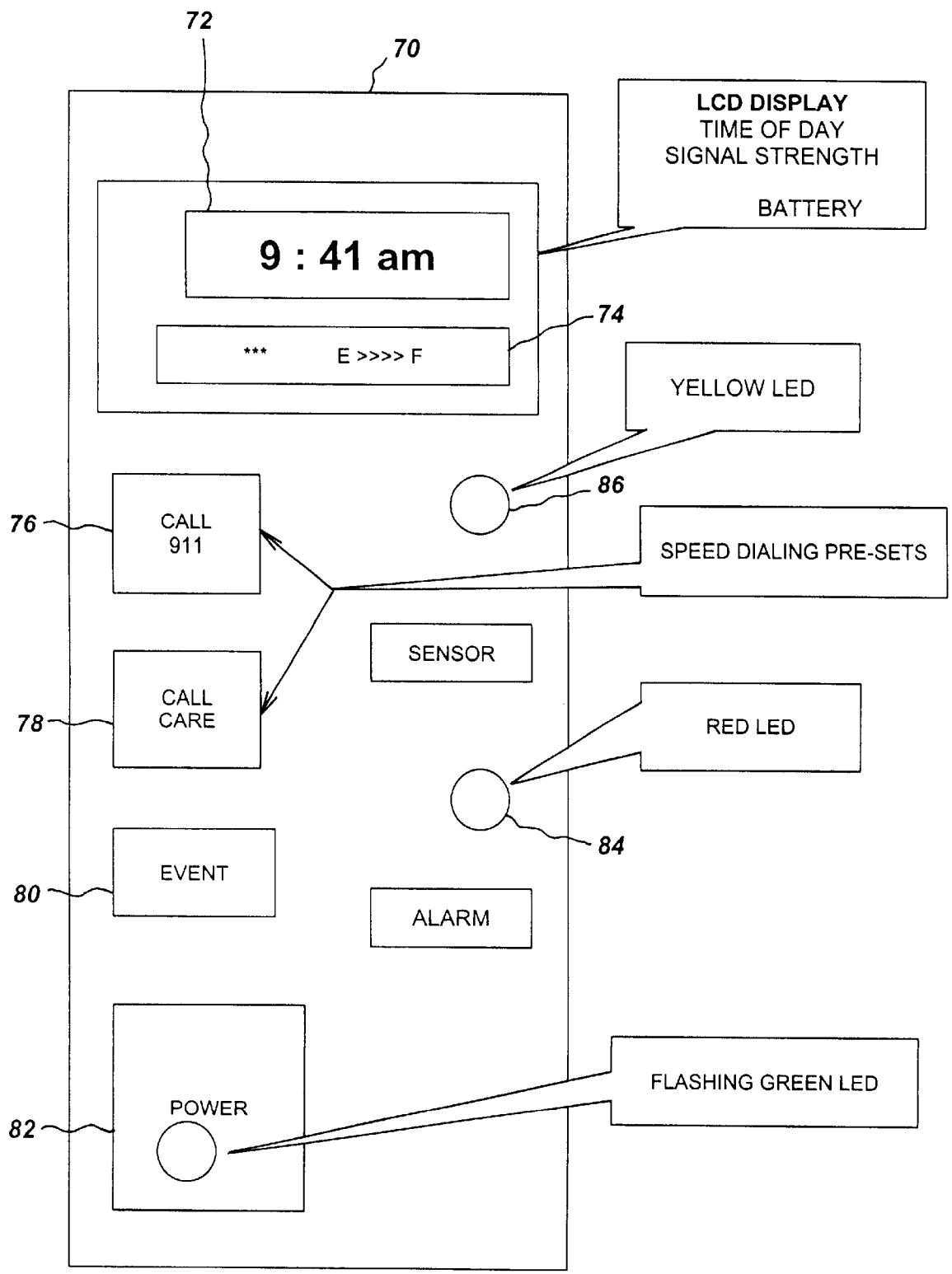
FIG. 3 illustrates a front panel drawing of the multi variable patient monitor portion of the WIBMS

Referring to FIG. 3, a front panel for the MVPM is illustrated. The MVPM has a time of day 72 and a battery strength indicator 74 which allows the wearer to determine if recharging or battery replacement is required. The panel 70 is dimensioned to be small and unobtrusive so that the wearer will not be disproportionately burdened by carrying the MPVM. The panel has several speed dialing preset buttons that allow emergency calls to 911 76 to be made and to call the care provider 78 simply by the press of a button. Similarly, if the wearer determines that an "event" has occurred such as faintness, shortness of breath, irregular heartbeat, or other symptoms, this event button 80 can be pressed and a signal generated associated with the event. A power indicator 82 is part of the panel so that the user can determine that power is "on." Sensor lamp 86 is on the panel as well to inform the user whether all sensors are operating or if a sensor has potentially become disconnected or has otherwise malfunctioned. An alarm light 84 together with an audible signal is also present on the control panel so that the patient can have both a visual and audible warning of any alarm condition that might exist.

The panel design shown in this FIG. 3 is by way of illustration only. It will be apparent to those skilled in the art that other panel designs are possible so long as the information is presented in an easy and useable way for the patient.

As noted above, the communications link between the MVPM and the care provider via the PSTN or the Internet is a bi-directional link. Thus requests for data from a workstation located at the care provider's location can be transmitted through the Internet to the MVPM. Data transfer (real time or stored) can be transferred from the MVPM through the Internet to various data bases for analysis or storage. Data from the MVPM can be transferred in real time or from storage through the Internet to other authorized users such as insurance providers. Alarm information is transferred from the MVPM to the care provider through the Internet or directly using a voice link. When a sensor malfunctions or becomes disconnected from the wearer, a "sensor off" signal is sent from the MVPM and transferred over the Internet to the medical care provider so that such information is available and so that the patient can be notified. Event information, as described earlier, may also be transferred to the medical care provider. The medical care provider can transmit a communication to disarm or reset alarms in the MVPM through the Internet as necessary. Further protocols relating to when and the type of bio-signal to be measured can be sent from the medical provider to the Internet over the MVPM. The personal emergency button for use by the user to activate a call to the medical care provider gives voice communication from the MVPM to and from the care provider. Real-time clock resets or any other variations in configuration of the MVPM can be transmitted from the medical care provider over the Internet to the MVPM.

A wireless Internet bio-telemetry system has now been illustrated. It is important to note that, while a particular wireless protocol was described in the preferred embodiment (i.e. CDMA) this is not meant as a limitation. For example other protocols for communication in a wireless network such as GSM or a PCS network will be equally suitable for use with the present invention. It is also anticipated that other types of wireless networks will also be suitable such as satellite networks and wireless local loop networks. The requirement is that there be two way communication with the MVPM and that internet connectivity flow as part of the communication system to allow interaction between health care provider and the patient via voice and via the Internet. It will be apparent to those skilled in the art that other variations in, for example and without limitation, the type of network, the type of bio-sensor, and the configuration of the patient monitor can be accomplished without departing from the scope of the invention as disclosed.

We claim:

1. A method for remotely monitoring a plurality of physiologic variables of a patient, comprising:

mounting a single-site bio-sensor, which is integrally placed within a mold, in an ear of said patient in a manner so as to allow sensing of signals representative of a plurality of physiologic variables of said patient;

sending said signals to a battery-powered, patient-worn monitoring unit;

processing said signals in said patient-worn monitoring unit to obtain processed data;

transmitting said data over a digital cellular telephone network to a second network, wherein said transmitting is performed using a wireless communication device built into said patient-worn monitoring unit; and transmitting said data over said second network to a health care provider terminal for presentation to a health care provider, and further comprising:

providing a microphone on said bio-sensor;

acquiring voice data from said patient using said microphone; and transmitting said voice data to said health care provider over said digital cellular telephone network using said wireless communication device built into said patient-worn monitoring unit.

2. The method of claim 1, wherein said bio-sensor is mounted so as to allow said patient to be ambulatory.

3. The method of claim 1, wherein said second network is the Internet.

4. The method claim 1, further comprising:

configuring a data collection protocol of said monitoring unit by communications from said healthcare provider terminal using said second network and said digital cellular telephone network.

5. The method of claim 4, wherein said protocol is selected from the group consisting of: alarm limits, data collection frequency, and data transmission frequency.

6. The method of claim 1, wherein said transmitting of said voice data to said health care provider comprises transmitting said voice data from said digital cellular telephone network to another network selected from the group consisting of: a public switched telephone network (PSTN) and an Internet.

7. The method of claim 6, wherein said transmitting of said voice data is bi-directional so as to provide health care provider voice data to said patient.

8. A system for remotely monitoring a plurality of physiologic variables of a patient, comprising:

a single-site bio-sensor integrally placed within a mold and adapted to fit in an ear of said patient in a manner so as to allow sensing of signals representative of a plurality of physiologic variables of said patient;

a battery-powered, patient-worn monitoring unit;

means for sending said signals to said patient-worn monitoring unit;

means for processing said signals in said patient-worn monitoring unit to obtain processed data;

a wireless communication device built into said patient-worn monitoring unit and configured to transmit said data over a digital cellular telephone network to a second network; and means for transmitting said data over said second network to a health care provider terminal for presentation to a health care provider, further comprising:

a microphone on said bio-sensor;

means for acquiring voice data from said patient using said microphone for supplying said voice data to said wireless communication device built into said patient-worn monitoring unit; and means in said wireless communication device for transmitting said voice data to said health care provider over said digital cellular telephone network.

9. The system of claim 8, wherein said bio-sensor comprises an ear-mounted sensor so as to allow said patient to be ambulatory.

10. The system of claim 8, wherein said second network comprises the Internet.

11. The system of claim 8, further comprising:

means for configuring a data collection protocol of said monitoring unit by communications from said healthcare provider terminal using said second network and said digital cellular telephone network.

12. The system of claim 11, wherein said protocol is selected from the group consisting of: alarm limits, data collection frequency, and data transmission frequency.

13. The system of claim 8, wherein said means in said wireless communication device provides for transmitting of said voice data to said health care provider over said digital cellular telephone network and another network selected from the group consisting of: a PSTN and an Internet.

14. The system of claim 13, wherein said means in said wireless communication device is further adapted for bi-directional transmitting so as to provide health care provider voice data to said patient.

* * * * *